United States Patent [19]

Quaghebeur et al.

[11] Patent Number: 5,491,124
[45] Date of Patent: Feb. 13, 1996

[54] HERBICIDAL COMPOSITIONS COMPRISING CHLOROACETAMIDE AND TRIKETONE HERBICIDES

[75] Inventors: Theo Quaghebeur, Saint-Symphorien; Walter Van Loocke, Meetkerke, both of Belgium

[73] Assignee: Sandoz Ltd., Basel, Switzerland

[21] Appl. No.: 262,725

[22] Filed: Jun. 20, 1994

[30] Foreign Application Priority Data

Jun. 25, 1993 [GB] United Kingdom ............ 9313210

[51] Int. Cl.⁶ .................. A01N 35/06; A01N 37/22; A01N 43/56; A01N 43/72
[52] U.S. Cl. ............. 504/139; 504/140; 504/149
[58] Field of Search ................ 504/341, 149, 504/139, 140

[56] References Cited

U.S. PATENT DOCUMENTS

| | | | |
|---|---|---|---|
| 4,759,794 | 7/1988 | Hsu | 71/93 |
| 4,869,748 | 9/1989 | Knudsen | 71/123 |

FOREIGN PATENT DOCUMENTS

| | | | |
|---|---|---|---|
| 230596 | 8/1987 | European Pat. Off. . | |
| 298679 | 1/1989 | European Pat. Off. . | |
| 298680 | 1/1989 | European Pat. Off. . | |
| 434613 | 6/1991 | European Pat. Off. . | |
| 8801977 | 11/1988 | United Kingdom | A01N 43/64 |
| 9105469 | 5/1991 | WIPO . | |
| 9113547 | 9/1991 | WIPO | A01N 41/10 |

OTHER PUBLICATIONS

*The Agrochemicals Handback* "Acetochlor", Propachlor 1987.
Wilson et al. Weed Technol 4(4) 731–738 (1990).
Proc. Ann. Mtg. Northeast Weed Sci. Assoc. 42 (1988) pp. 3–5.

*Primary Examiner*—S. Mark Clardy
*Attorney, Agent, or Firm*—Allen E. Norris

[57] ABSTRACT

Co-application of certain chloroacetamide herbicides with certain triketone herbicides provides improved herbicidal activity.

12 Claims, No Drawings

HERBICIDAL COMPOSITIONS COMPRISING CHLOROACETAMIDE AND TRIKETONE HERBICIDES

The present invention concerns a method of controlling undesired plant growth employing co-application of at least one herbicide from the class of the chloroacetamides and at least one herbicide from the class of the triketones. Further the invention also concerns compositions comprising at least one herbicidal chloroacetamide and at least one herbicidal triketone for controlling undesired plant growth.

Herbicidal chloroacetamides are well known from literature and are to a large extent commercially available, and are also applied in agriculture. Examples for herbicidal chloroacetamides are inter alia; Acetochlor (HARNESS®) whose chemical designation is 2-chloro-N-(ethoxymethyl)-N-(2-ethyl-6-methylphenyl)-acetamide: Metolachlor (DUAL®) whose chemical designation is 2-chloro-6'-ethyl-N-(2-methoxy-1-methylethyl)acet-o-toluidide; and Metazachlor (BUTISAN S®) whose chemical designation is 2-chloro-N-(pyrazol-1-ylmethyl)acet-2',6'-xylidide.

Herbicidal triketones have been described in the literature, e.g. in EP-A-338992, EP-A-336898, U.S. Pat. No. 4,869,748, EP-A-186118, EP-A-186119, EP-A-186120, U.S. Pat. Nos. 4,695,673, 4,921,526, 5,006,150, 5,089,046, EP-A-249150, EP-A-137963, EP-A-394889 or EP-A-506907. Examples for herbicidal triketones are inter alia Sulcotrione (MIKADO®) whose chemical designation is 2-(2-chloro-4-methanesulfonylbenzoyl)-1,3-cyclohexandione; 2-(4-methylsulfonyloxy-2-nitrobenzoyl)-4,4,6,6-tetramethyl-1,3-cyclohexanedione; 3-(4-methylsulfonyloxy-2-nitrobenzoyl)-bicyclo-[3,2,1]octane-2,4-dione; 3-(4-methylsulfonyl-2-nitrobenzoyl)-bicyclo-[3,2,1]octane-2,4-dione; 4-(4-chloro-2-nitrobenzoyl)-2,6,6-trimethyl-2H-1,2-oxazine-3,5(4H, 6H)-dione; 3-(4-methylthio-2-nitrobenzoyl)-bicyclo[3,2,1]octane-2,4-dione; 4-(2-nitro-4-trifluoromethoxybenzoyl)2,6,6-trimethyl-2H-1,2-oxazine-3,5(4H, 6H)-dione.

It has now surprisingly been found that co-application of at least one chloroacetamide and at least one triketone results in better and in some cases longer-lasting control of undesired plant growth. This synergistic effect exhibits itself as a high degree of control at co-application rates which are significantly lower than the rate of each individual compound required to obtain the same degree of control. Furthermore, at any given co-application rate the degree of control is higher than the additive effect obtained for the individual components at the same rate. In some cases simultaneously the speed of activity and the level of control are enhanced. In some cases weeds can be controlled which are not controlled by either component at economical rates.

This synergistic effect allows satisfactory control at reduced application rates for each component and even at levels which if applied for a particular component alone would give insufficient control. Additionally, longer residual control may be achieved. This provides for significant economic and environmental advantages in the use of the chloroacetamide(s) and the triketone(s) used in combination therewith.

Co-application can be achieved using tank mixes of preformulated individual active ingredients, simultaneous or sequential (preferably 1–2 days) application of such formulation or application of preformulated fixed pre-mix combinations of the individual active ingredients.

The co-application of the combination of chloroacetamide(s) and triketone(s) according to present invention is especially suitable in crops of monocotyledones, such as cereals, maize and rice. However, application in maize crops being infested with monocotyledonous and dicotyledonous weeds is most advantageous, as harmful effects against the crop plants are not enhanced. Both pre- and postemergence applications to the undesired weeds is possible with the combination of the invention. However, the preferred time point of application in maize is after emergence of the maize seedlings.

The present invention therefore concerns a method of combatting or controlling undesired plant growth or otherwise regulating plant growth which comprises co-applying to a locus where such combatting or control is desired an herbicidally or plant growth regulating effective aggregate amount of at least one chloroacetamide and at least one triketone.

As a special embodiment of the invention the controlling of undesired mono- and dicotyledonous weeds in maize with post-emergence application has to be mentioned.

Application rates for co-application will of course vary depending upon climatic conditions, season, soil ecology, weeds to be combatted and the like, however, successful results can be obtained e.g. with rates of the chloroacetamide of 0.1 to 4 kg/ha, preferably 0.5 to 3.5 kg/ha, especially 1.5 to 3 kg/ha in co-application with rates of the triketone which are significantly lower than recommended for use thereof individually; e.g. 0.01 to 2 kg/ha, preferably 0.1 to kg/ha, especially 0.1 to 0.6 kg/ha. For example the specific application rates of the chloroacetamide component is 0.9 to 3.4 kg/ha for Acetochlor, 1.4 to 3.4 kg/ha for Metolachlor, and 0.75 to 1.5 kg/ha for Metazachlor. The application rate for Sulcotrione as a component for co-application is 0.15 to 0.45 kg/ha.

The suitability of specific co-applications for pre- or post-emergent uses and selectively will of course depend on the partners chosen.

The invention also provides herbicidal or plant growth regulating compositions comprising an herbicidally effective aggregate amount of at least one chloroacetamide herbicide and at least one triketone herbicide.

Such compositions contain the active substances in association with agriculturally acceptable diluents. They may be employed in either solid or liquid forms e.g. in the form of a wettable powder or an emulsifiable concentrate, incorporating conventional diluents. Such compositions may be produced in conventional manner, e.g. by mixing the active ingredient with a diluent and optionally other formulating ingredients such as surfactants and oils.

The term diluents as used herein means any liquid or solid agriculturally acceptable material which may be added to the active constituent to provide a more easily or improved applicable form, or to achieve a usable or desirable strength of activity. Examples of diluents are talc, kaolin, diatomaceous earth, xylene, non-phytotoxic oils, or water.

Particular formulations, to be applied in spraying forms such as water dispersible concentrates or wettable powders, may contain surfactants such as wetting and dispersing agents, e.g. the condensation product of formaldehyde with naphthalene sulphonate, an alkylarylsuphonate, a lignin sulphonate, a fatty alkyl sulphate, an ethoxylated alkylphenol or an ethoxylated fatty alcohol.

In general, the formulations include from 0.01 to 90% by weight of active agent(s) and from 0 to 20% by weight of agriculturally acceptable surfactant, the active agent consisting of at least one chloroacetamide and at least one triketone. Concentrate forms of compositions generally contain between about 2 and 90%, preferably between about 5 and 80% by weight of active agent. Application forms of formulation may for example contain from 0.01 to 20% by weight of active agent.

When employing concurrent, immediately sequential or tank mix applications the herbicide partner(s) can be employed in commercially available form if appropriate and at rates equivalent to or preferably below those recommended by the manufacturer or in the references cited above.

On co-application according to the present invention other compounds having biological activity, e.g. compounds having insecticidal or fungicidal activity, or fertilizers such as ammonium containing fertilizers, may also be included.

In another aspect of present invention the combination of a chloroacetamide herbicide and a triketone herbicide may also comprise a further herbicide. The triazine-herbicides have proven as especially suitable for this purpose. Examples are atrazine, simazine, cyanazine, prometon, ametryn, prometryn, hexazinone, or metribuzin. Especially preferable is the addition of atrazine. Examples for such 3-way mixes are combination like sulcotrione/acetochlor/atrazine, or sulcotrione/metolachlor/atrazine.

The preferred mode of application is tank mix prepared e.g. by adding the chloroacetamide to a tank containing the triketone partner and an appropriate surfactant or vice versa depending on the type of herbicide partner chosen. It is advisable to consult labels of mixing partners and to conduct compatibility tests prior to mixing.

Depending on the choice of co-application partners both pre- and post-emergence activity on a large range of broadleaf and grassy weeds may be achieved.

Preferred combinations of herbicides according to present inventions are those wherein the chloroacetamide is selected from Acetochlor and Metolachlor.

On the other hand those combinations are preferred wherein the triketone is selected from 4-(4-chloro-2-nitrobenzoyl)-2,6,6-trimethyl-2H-1,2-oxazine-3,5-(4H, 6H) dione, and Sulcotrione, with Sulcotrione being preferred.

Most preferred combinations are those of Sulcotrione with Acetochlor or Metolachlor. The mixture ratios and application rates will be determinable according to the specific soil, crop and climate conditions of use. As an example co-application rates will be in the range of 0.9 to 3.4 kg/ha of Acetochlor or 1.4 to 3.4 kg/ha of Metolachlor, and 0.15 to 0.45 kg/ha of Sulcotrione. The ratios of the active ingredients in the compositions by weight of Sulcotrione and Acetochlor is between 1:2 and 1:25, and for Sulcotrione and Metolachlor between 1:3 and 1:25.

Crop selectivity will also usually depend upon choice of partners. Excellent selectivity may be achieved with the mixtures of this invention for example in maize, soybean and several other crops.

BIOLOGICAL TEST METHOD

Active ingredients were weighed and dissolved in a stock solution consisting of acetone:deionized water, 1:1, and 0.5% adjuvant mixture consisting of surfactants SPAN® 20:TWEEN® 20:TWEEN® 85, 1:1:1. Dilutions from this stock solution are performed to allow for preparation of spray solutions consisting of single doses of individual or combined active ingredients. Each dose is applied simultaneously via a linear track sprayer set to deliver 600 liters/ha spray volume to the foliage of the selected weed seedling species, postemergence application. The seedlings used are cultured to develop plants at the two- to early three-leaf stage. The stage of development of each seedling at application time is recorded. After application, the treated plants are transferred to the greenhouse and held until termination of the experiment within four weeks. Symptoms of injury are recorded two and ten days after postemergence application. Visual percentage ratings for weed control are taken nineteen days after postemergence application.

Co-application of chloroacetamide(s) with triketone(s) such as outlined above produces improved herbicidal effects compared with application of each active ingredient alone.

The following results were obtained:

| Herbicide and Weed | Rate (g AI/ha) | | Percent Phytotoxicity | | |
|---|---|---|---|---|---|
| | Sulcotrione | Acetamide | Sulcotrione | Acetamide | Combination |
| Metolachlor | | | | | |
| Abutilon theophrasti | 100 | 750 | 80 | 10 | 95 |
| | 100 | 1500 | 80 | 0 | 100 |
| Amaranthus retroflexus | 100 | 1500 | 50 | 20 | 80 |
| | 200 | 1500 | 60 | 20 | 90 |
| Avena fatua | 50 | 375 | 0 | 0 | 20 |
| | 100 | 375 | 0 | 0 | 20 |
| | 200 | 375 | 30 | 0 | 60 |
| Acetochlor | | | | | |
| Abutilon theophrasti | 100 | 500 | 100 | 0 | 98 |
| | 100 | 1000 | 100 | 0 | 98 |
| Amaranthus retroflexus | 50 | 1000 | 40 | 20 | 70 |
| | 100 | 1000 | 70 | 20 | 80 |
| Avena fatua | 50 | 1000 | 10 | 80 | 100 |
| | 100 | 1000 | 40 | 80 | 100 |
| | 200 | 1000 | 20 | 80 | 95 |

At the tested concentrations the combination of Sulcotrione with Metolachlor or Acetochlor exhibited synergistic enhancements of the herbicidal effects.

FIELD TEST a) France

Small field units in a maize field, infested with grassy and broad-leaved weeds are sprayed with a tank-mix suspension of Acetochlor and Sulcotrione. The stage of the grassy weeds was "full tillering" and "8-leaves stage" for the broad-leaved weeds. The lot size was 8 meters in length and 3 meters in broadth. The application rates are 0.96 kg/ha of Acetochlor and 0.21 kg/ha of Sulcotrione. Thirty to fifty days after treatment the efficacy is evaluated, both as control of the weeds and as tolerance of the crop plants.

Site A

Crop: Maize, variety Adonis
Weeds: *Digitaria sanguinalis:* 50 plants/m²
*Solanum nigrum:* 50 plants/m²

| Treatment | g AI/ha | overall weed control 45 days after application | expected additive effect | synergistic effect |
|---|---|---|---|---|
| Sulcotrione | 210 | 20% | — | — |
| Acetochlor | 960 | 0% | — | — |
| Acetochlor + Sulcotrione | 960 + 210 | 50% | 20% | +30% |

No damage was observed with the crop plants.

Site B

Crop: Maize, variety Santana
Weeds: *Echinochloa cms galli:* 25 plants/m²
*Digitaria sanguinalis:* 6 plants/m²

| Treatment | g AI/ha | overall weed control 30 days after application | expected additive effect | synergistic effect |
|---|---|---|---|---|
| Sulcotrione | 210 | 20% | — | — |
| Acetochlor | 960 | 0% | — | — |
| Acetochlor + Sulcotrione | 960 + 210 | 55% | 20% | 35% |

No damage was observed with the crop plants.

b) Belgium

Small field units in a maize field, infested with *Echinochloa crus galli* and *Solanum nigrum* are sprayed with a tank-mix suspension of Metolachlor, Atrazine and Sulcotrione. The stage of the weeds was "4-leaves-stage" for *Echinochloa crus galli* and "8–10 leaves-stage" for *Solanum nigrum*. The lot size was 8 meters in length and 3 meters in broadth. The application rates are 1.60 kg/ha of Metolachlor, 0.75 kg/ha of Atrazine and 0.15 kg/ha of Sulcotrione. Fourteen days after treatment the efficacy is evaluated, both as control of the weeds and as tolerance of the crop plants.

The results (in percentage control) were as follows:
Crop: Maize
Weeds: *Echinochloa crus galli:* 4 leaves stage
*Solanum nigrum:* 8–10 leaves stage
Efficiency at 14 days after application, percentage of control

| g AI/ha | | *Solanum nigrum* | *Echinochloa c.g.* |
|---|---|---|---|
| Sulcotrione | 360 | 81% | 46% |
| Sulcotrione + | 150 | 76% | 43% |
| Atrazine | 750 | | |
| Sulcotrione + | 150 | 100% | 96% |
| Atrazine + | 750 | | |
| Metolachlor | 1600 | | |

No damage was observed with the crop plants.

What is claimed is:

1. A method of controlling undesired plant growth which comprises co-application to the locus of the said undesired plant growth at least one chloroacetamide herbicide selected from acetochlor and metazachlor and at least one triketone herbicide selected from sulcotrione, 2-(4-methylsulfonyloxy-2-nitrobenzoyl)-4,4,6,6-tetramethyl-1,3-cyclohexandione; 3-(4-methylsufonyloxy-2-nitrobenzoyl)-bicyclo-[3,2,1]octane-2,4-dione; 3-(4-methylsulfonyl-2-nitrobenzoyl)-bicyclo-[3,2,1]octane-2,4-dione; 4-(4-chloro-2-nitrobenzoyl)-2,6,6-trimethyl-2H-1,2-oxazine-3,5(4H,6H)-dione; 3-(4-methylthio-2-nitrobenzoyl)-bicyclo[3,2,1] octane- 2,4-dione; 4-(2-nitro-4-trifluoromethoxybenzoyl)-2,6,6-trimethyl-2H-1,2-oxazine-3,5(4H,6H)dione in herbicidally effective aggregate amount.

2. A method according to claim 1 wherein the amount of chloroacetamide is from 0.1 to 4.0 kg/ha.

3. A method according to claim 1 wherein the amount of triketone is form 0.01 to 2 kg/ha.

4. A method according to claim 1 wherein the triketone is selected from 4-(4-chloro-2-nitrobenzoyl)-2,6,6-trimethyl-2H-1,2-oxazine-3,5-(4H,6H)dione and sulcotrione.

5. A method according to claim 1 wherein acetochlor and sulcotrione are applied.

6. A method according to claim 1 wherein atrazine is co-applied as additional herbicidal component.

7. A method according to claim 1 wherein co-application is post-emergence on maize crops.

8. A herbicidal composition comprising a herbicidally effective aggregate amount of at least one chloroacetamide herbicide selected from acetochlor and metazachlor and at least one triketone herbicide selected from sulcotrione, 2-(4-methylsulfonyloxy-2-nitrobenzoyl)-4,4,6,6-tetramethyl-1,3-cyclohexandione; 3-(4-methylsufonyloxy-2-nitrobenzoyl)-bicyclo-[3,2,1]octane-2,4-dione; 3-(4-methylsulfonyl-2-nitrobenzoyl)-bicyclo-[3,2,1]octane-2,4-dione; 4-( 4-chloro-2-nitrobenzoyl)-2,6,6-trimethyl-2H-1,2-oxazine-3,5(4H, 6H)-dione; 3-(4-methylthio-2-nitrobenzoyl)-bicyclo[ 3,2,1] octane-2,4-dione; 4-(2-nitro-4-trifluoromethoxybenzoyl)-2, 6,6-trimethyl-2H-1,2-oxazine-3,5(4H,6H)dione.

9. A composition according to claim 8 wherein the chloroacetamide is acetochlor.

10. A composition according to claim 8 wherein the triketone is selected from 4-(4-chloro-2-nitrobenzoyl)-2,6, 6-trimethyl-2H-1,2-oxazine-3,5-(4H,6H)dione and sulcotrione.

11. A composition according to claim 8 which comprises acetochlor and sulcotrione.

12. A composition according to claim 8 which comprises atrazine as additional herbicidal component.

\* \* \* \* \*